United States Patent [19]

Brunelli et al.

[11] Patent Number: 5,324,878
[45] Date of Patent: Jun. 28, 1994

[54] PROCESS FOR CATALYTIC DIMERIZATION OF ISOBUTENE

[75] Inventors: Maurizio Brunelli, San Donato Milanese; Walter Castelvetro, San Giuliano Milanese; Carlo Perego, Carnate; Stefano Peratello, Nova Milanese, all of Italy

[73] Assignees: Eniricerche S.p.A.; Euron S.p.A., Milan, Italy

[21] Appl. No.: 955,472

[22] Filed: Oct. 2, 1992

[30] Foreign Application Priority Data

Oct. 4, 1991 [IT] Italy .................. MI91-A/002650

[51] Int. Cl.$^5$ .................................. C07C 2/02
[52] U.S. Cl. ........................ 585/508; 585/510; 585/520; 585/533; 585/666
[58] Field of Search .......... 585/575, 639, 824, 934, 585/952, 508, 510, 520, 533, 666

[56] References Cited

U.S. PATENT DOCUMENTS

| | | |
|---|---|---|
| 3,325,472 | 6/1967 | Jones et al. |
| 3,518,323 | 6/1970 | Pine et al. |
| 3,760,026 | 9/1973 | Reusser et al. ............... 585/316 |
| 5,049,536 | 9/1991 | Bellussi et al. ............... 502/235 |

FOREIGN PATENT DOCUMENTS

| | | |
|---|---|---|
| 0132172 | 1/1985 | European Pat. Off. |
| 0133052 | 2/1985 | European Pat. Off. |
| 0224220 | 6/1987 | European Pat. Off. |
| 0340868 | 11/1989 | European Pat. Off. |
| 1171950 | 11/1969 | United Kingdom |

*Primary Examiner*—Patrick P. Garvin
*Assistant Examiner*—Brent M. Peebles
*Attorney, Agent, or Firm*—George P. Hoare, Jr.

[57] ABSTRACT

Disclosed is a process for carrying out the selective dimerization of isobutene in order to produce alpha- and beta-di-isobutene dimer$_3$, according to which process an isobutene stream is brought into contact, under dimerization conditions, with a solid silica gel/alumina catalyst which is amorphous when analyzed by X-ray diffraction, displays a molar ratio of $SiO_2/Al_2O_3$ comprised within the range of from 30:1 to 500:1, has a surface-area comprised within the range of from 500 to 1000 m$^2$/g, a porosity of from 0.3 to 0.6 ml/g and an average pore diameter of approximately 10 Å (Ångstrom), and is free from pores with a larger diameter than 30 Å.

8 Claims, No Drawings

PROCESS FOR CATALYTIC DIMERIZATION OF ISOBUTENE

The present invention relates to a process for carrying out the selective dimerization of isobutene.

The processes known from the prior art, used in order to dimerize isobutene, are generally based on the use of an acidic catalyst, such as, e.g., sulfuric acid, polyphosphoric acid (either in free form, or supported on an inorganic solid carrier); heteropoly-acids, such as phosphomolybdic acid and silicotungstic acid; acidic ion-exchange resins, of polystyrenesulfonic or fluorosulfonic types; complexes of boron trifluoride which alcohols, organic acids, esters, ethers or ketones; aluminum trichloride associated with ethyl ether, hydrogen chloride or nitromethane; simple or complex salts, in particular nickel salts activated with an alkyl-aluminum or alkyl-aluminum halide; and metal oxides, such as bismuth oxide possibly associated with phosphorus oxide.

Other dimerization catalysts known from the prior art are aluminosilicates and zeolites, possibly modified with salts or oxides of such metals as nickel, chrome and cobalt, such as disclosed, e.g., in U.S. Pat. Nos. 3,518,323 and 3,325,465; in European patent Application Publ. Nos. 132,172; 224,220; and 133,052; and in U.K. patent 1,171,950.

A large number of the dimerization catalysts known from the prior art essentially display the drawbacks deriving from the corrosiveness of the acids used, the need for disposing of the spent catalysts, a short service life and/or the complexity and cost of their preparation. A problem shared by all of these catalysts known from the prior art consists in the poor selectivity to the desired reaction products. Thus, in their use in isobutene dimerization, said known catalysts cause the formation of considerable amounts of higher oligomers, and of different isomers than the more valuable ones, i.e., alpha- and beta-diisobutene. Finally, when a stream of isobutene mixed with other $C_4$ olefins is submitted to dimerization, codimers are normally formed.

Such codimers are thought to be formed owing to the relatively high temperatures at which the catalysts known from the prior art display their activity, or to the excessively high acidity of said catalysts, which favours phenomena of molecular rearrangement, or other, undesired side reactions.

In European patent Application published with No. 340,868, an amorphous, microporous silica/alumina gel is disclosed which is active in processes of isomerization, alkylation, dewaxing and dimerization of linear olefins.

The present Applicant found now, according to the present invention, that the particular silica/alumina gel disclosed in said European patent Application 340,868 constitutes a highly active catalyst for isobutene dimerization, which catalyst is essentially free from any activities leading to isomerization of reactants and dimerization products.

In particular, the present Applicant found that such a silica gel is capable of causing isobutene to undergo dimerization leading to alpha- and beta-diisobutene, with an unexpectedly high selectivity. It enables possible valuable products for preparing high antiknock value gasolines, or for use as chemical intermediates, to be obtained in a simple and cheap way.

In accordance therewith, the present invention relates to a process for dimerizing isobutene into alpha- and beta-di-isobutene dimers, characterized in that an isobutene stream is brought into contact, under dimerization conditions, with a solid silica/alumina gel catalyst which is amorphous when analysed by X-ray diffraction, displays a molar ratio of $SiO_2/Al_2O_3$ comprised within the range of from 30:1 to 500:1, has a surface-area comprised within the range of from 500 to 1000 $m^3/g$, a porosity of from 0.3 to 0.6 ml/g and an average pore diameter of approximately 10 Å (Ångstrom), and is free from pores with a larger diameter than 30 Å.

In the preferred form of practical embodiment, said silica/alumina gel shows a molar ratio of $SiO_2/Al_2O_3$ of the order of 100:1, a surface-area of the order of 800:1 $m^2/g$, and a porosity of the order of 0.4–0.5 ml/g.

When it is used as a catalyst, said silica/alumina gel is supported on a suitable solid, inert carrier material, or is mixed with an inert, solid material. In particular, said gel can be mixed with suitable metal oxides essentially performing the function of binding agents. Suitable oxides for the intended purpose are aluminas, silicas, and titanium, magnesium and zirconium oxides. The gel and the binding agent can be mixed in amounts, by weight, comprised within the range of from 50:50 to 95:5, and preferably of from 30:90 to 90:10. Both components can be mixed by means of conventional techniques, and the resulting mixture is suitably densified into the desired end shape, for example as extrudates or granulates. By operating in that way, the catalyst can be given improved mechanical characteristics.

The reaction of dimerization of isobutene can be carried out in continuous, semi-continuous and batchwise modes, by operating in liquid phase, gas phase or mixed (liquid-gas) phase.

When the process is carried out in batchwise mode, a catalyst amount of from 1 to 50% by weight relative to isobutene, a temperature of from 50° to 150° C., and preferably of from 55° to 80° C., and a pressure of from 1 to 200 abs.atm and preferably of from 1 to 6 abs.atm, are used.

For continuous or semicontinuous processes, the reaction is advantageously carried out at a temperature of from 50° to 200° C. and preferably of from 50° to 150° C., and with an isobutene hourly space velocity (WHSV) comprised within the range of from 0.5 to 8 hours$^{-1}$. In any case, pure isobutene, or isobutene mixed with other hydrocarbons, in particular $C_4$ hydrocarbons, can be used.

The dimerization reaction is an exothermic one and therefore the inner temperature in the reactor should be controlled, in order to prevent an excessive increase in said temperature that may lead to the formation of higher oligomers, and/or to undesired isomerization phenomena.

In particular, isobutene dimerization proceeds with the above said isobutene dimer isomers being formed, i.e., 2,4,4-trimethyl-1-pentene (alpha-diisobutene) and 2,4,4-trimethyl-2-pentene (beta-diisobutene).

These dimers can be used as chemical intermediates for the preparation of nonionic surfactants, crosslinking agents for elastomers, plasticizers, and so forth, by means of alkylating, aminating or carbonylating reactions.

Furthermore, alpha- and beta-diisobutene are useful in the preparation of high antiknock value gasolines, because they display the following ROM and MON (lead-less) values: RON=106 and MON=86.5 (alpha isomer); and RON=103.5 and MON=86.2 (beta isomer), and can be hydrogenated to yield isooctane (2,2,4-trimethyl-pentane), having RON=100 and MON=100.

The silica/alumina gel used as the catalyst in the process according to the present invention can be prepared according to a process comprising:
(i) preparing an aqueous solution of a water-soluble aluminum compound, capable of yielding $Al_2O_3$ by hydrolysis, a water-soluble silicon compound capable of yielding $SiO_2$ by hydrolysis and a tetra-alkyl-ammonium hydroxide, wherein the alkyl is selected from ethyl, n-propyl and n-butyl;
(ii) heating the resulting solution in order to cause it to undergo gelation; and
(iii) drying the gel and calcining it, by operating under an atmosphere which is firstly inert and subsequently oxidizing.

The aluminum compounds used in the process preferably are aluminum trialkoxides, such as, e.g., aluminum tri-n-propoxide and aluminum tri-isopropoxide, silicon compounds preferably are tetraalkyl silicates, such as, e.g., tetraethyl silicate. These reactants are advantageously used in such a ratio to each other as to have the desired composition for the gel obtained eventually, on considering that the reaction yield practically is quantitative.

The step (ii) gelation is carried out at a temperature comprised within the range of from 50° to 70° C. and preferably of the order of 60° C. Under these conditions, the required time for a complete gelation may vary from about 15 minutes to about 5 hours, as a function of the selected operating temperature and, in the preferred form of practical embodiment, is of the order of 25-60 minutes.

The step (iii) drying is advantageously carried out at a temperature lower than about 150° C., and preferably of the order of 90°-100° C., for a long enough time in order to remove water to a complete or substantially complete extent. The calcination is carried out under an atmosphere which initially is an inert atmosphere (e.g., nitrogen) and then is an oxidizing atmosphere (e.g., air), at temperatures ranging from 500° to 700° C. and preferably of the order of 550°-600° C., within calcination times which may range from 4 to 20 hours, as a function of the selected operating temperature and, in the preferred form of practical embodiment, of the order of 6-16 hours.

The following experimental examples are reported in order to illustrate the present invention in greater detail.

EXAMPLE 1

Catalyst preparation 2 g of aluminum isopropoxide is dissolved, at room temperature, in 68.5 g of an aqueous solution of tetra-propyl-ammonium hydroxide (TPA-OH) at 13.35% by weight. The solution is heated to 60° C., and 104.1 g of tetraethyl silicate (TES) is added. The resulting mixture displays the following molar ratios:
$SiO_2/Al_2O_3 = 102:1$;
$TPA-OH/SiO_2 = 0.09:1$; and
$H_2O/SiO_2 = 15:1$.

This mixture is kept 40 minutes at 60° C., with stirring, until a homogeneous gel is obtained, which is dried under an air stream at 90° C. and then is calcined at 550° C. initially under a nitrogen stream, for 3 hours, and then under an air stream, for 10 hours.

A silica/alumina gel is obtained, with a quantitative yield as referred to the initially charged raw materials. Said gel is granulated into particles of 1-2 mm of size.

The resulting catalyst displays the following characteristics:
The catalyst is amorphous when examined by X-ray diffraction, carried out on the catalyst in powder form, on a Philips vertical goniometer, by using Cu K-alpha radiation);
Ratio of $SiO_2/Al_2O_3 = 100$, by mol;
Surface-area = 800 $m^2/g$ (as measured by the B.E.T. method, by means of Carlo Erba Sorptomatic 1800 apparatus);
Porosity = 0.44 ml/g, with average pore diameter of about 10 Å, and no pores with larger diameter than 30 Å (values as determined by means of Carlo Erba Sorptomatic apparatus).

EXAMPLE 2

A glass ampul, flame welded under nitrogen atmosphere, containing 2.14 g of the catalyst prepared in Example 1, finely ground in a mortar and kept heated at 550° C. for 6 hours, is charged to a 200-ml autoclave. The autoclave is evacuated, is charged with a pressure of 1 abs.atm of nitrogen, and then 15 g of isobutene is charged to it, by low-temperature condensation. The temperature of the autoclave is subsequently increased up to 60° C. by dipping in an oil bath.

The reaction of isobutene dimerization is initiated by breaking the catalyst containing ampul by means of the mechanical stirrer with which the autoclave is equipped. Dimerization is a strongly exothermic reaction, and the actual reaction temperature, which is monitored by means of a thermocouple installed inside the autoclave, rises up to 80° C. within 5-10 seconds and is kept controlled at this value, by means of the bath, with a temperature fluctuation of ±2° C. During the whole course of the reaction, the pressure inside the interior of the autoclave is essentially due to the vapour pressure of unreacted isobutene. As a consequence, the pressure decreases owing to the disappearing of the liquid isobutenic phase, followed by the progressive disappearing of its vapour phase.

Samples of the reaction mixture are collected from the autoclave at different times, through a dipleg, and are condensed inside large test tubes for the subsequent analyses. During the whole course of the reaction, the reaction mixture is kept vigorously stirred by means of a mechanical stirrer, in order to secure a good contact between the liquid phase and the solid phase (i.e., the catalyst), besides a good homogeneity of the mixture during sample withdrawal.

The values of conversion and the quantitative analysis of the products contained in the mixtures corresponding to the various samples collected is carried out by gas-chromatographic means, using a Hewlett Packard wide bore column gas-chromatograph with an apolar stationary phase RSL300, at a programmed temperature from 30° to 280° C.

The quantitative determination of the different isomers of isobutene dimer—i.e., 2,4,4-trimethyl-1-pentene (alpha-diisobutene) and 2,4,4-trimethyl-2-pentene (beta-diisobutene) is also carried out by gas-chromatographic means, using a capillary column with apolar stationary phase SPB1 which allows them to be separated, and their structural identification is carried out on a mixture containing 96% of dimer, obtained by fractional distillation of the first fraction collected during the reaction, by means of a mass spectrometer coupled with a capillary-column gas-chromatograph, and on the basis of $^1H$ and $^{13}C$ N.M.R. patterns. The results are reported in Table 1.

EXAMPLE 3

The process is carried out as in Example 2, with 1.5 g of the same catalyst as of Example 2, reactivated by heating at 550° C. for 6 hours, and 12 g in isobutene. In this case, the reaction is initiated as soon as the inner temperature inside the autoclave reaches the value of 55° C., so as to have a less violent heat development than in Example 2. In that way, the inner temperature in the autoclave reaches the oil bath temperature (60° C.) within a shorter time than 30 seconds, and reaches a peak value of about 65° C. after 2 minutes, and then decreases down to 60° C.

The results of this example are reported in Table 1.

TABLE 1

| Example | | 2 | 3 |
|---|---|---|---|
| Temperature (°C.) | | 80 | 60–65 |
| Catalyst (% by weight) | | 14 | 12 |
| Isobutene conversion (%) | | | |
| | 2 minutes | 78 | 55 |
| | 9 minutes | — | 85 |
| Composition, oligomers (%) | | | |
| $C_8$ | 2 minutes | 52 | 73 |
| | 9 minutes | — | 62 |
| $C_{12}$ | 2 minutes | 44 | 26 |
| | 9 minutes | — | 33 |
| $C_{16}+$ | 2 minutes | 4 | 1 |
| | 9 minutes | — | 5 |
| Dimer composition | | | |
| alpha-isomer | 2 minutes | 77 | 85 |
| | 9 minutes | — | 73 |
| beta-isomer | 2 minutes | 21 | 14 |
| | 9 minutes | — | 17 |
| other isomers | 2 minutes | 2 | 1 |
| | 9 minutes | — | 10 |

We claim:

1. Process for dimerizing isobutene into alpha- and beta-di-isobutene dimers, said process comprising contacting an isobutene stream, under dimerization conditions, with a solid silica/alumina gel catalyst which is amorphous when analysed by X ray diffraction, displays a molar ratio of $SiO_2/Al_2O_3$ comprised within the range of from 30:1 to 500:1, has a surface-area comprised within the range of from 500 to 1000 $m^2/g$, a porosity of from 0.3 to 0.6 ml/g and an average pore diameter of approximately 10 Å (Ångstrom), and is free from pores with a diameter larger than 30 Å.

2. Process according to claim 1, wherein said silica/alumina gel shows a molar ratio of $SiO_2/Al_2O_3$ of the order of 100:1, a surface-area of the order of 800:1 $m^2/g$, and a porosity of the order of 0.4–0.5 ml/g.

3. Process according to claim 1, wherein said silica/alumina gel is supported on a solid, inert carrier material, or is mixed with an inert, solid material.

4. Process according to claim 1, wherein the reaction of isobutene dimerization is carried out in batchwise mode, with a catalyst amount of from 1 to 50% by weight relatively to isobutene, at a temperature of from 50° to 150° C., and under a pressure of from 1 to 200 abs.atm.

5. Process according to claim 1, wherein the isobutene dimerization reaction is carried out in continuous mode at a temperature of from 50° to 200° C., and with an isobutene hourly space velocity (WHSV) comprised within the range of from 0.5 to 8 hours$^{-1}$, using pure isobutene, or isobutene mixed with other olefins and/or paraffins.

6. A process according to claim 4, wherein the temperature is from 55° to 80° C.

7. A process according to claim 4, wherein the pressure is from 1 to 6 abs.atm.

8. A process according to claim 5, wherein the temperature is from 50° to 150° C.

* * * * *